United States Patent
Sasaki et al.

(10) Patent No.: US 11,723,628 B2
(45) Date of Patent: Aug. 15, 2023

(54) INFORMATION PROCESSING APPARATUS, INFORMATION PROCESSING METHOD, NON-TRANSITORY COMPUTER READABLE STORAGE MEDIUM, AND ULTRASONIC DIAGNOSIS APPARATUS

(71) Applicant: CANON KABUSHIKI KAISHA, Tokyo (JP)

(72) Inventors: Shoya Sasaki, Kanagawa (JP); Naoya Iizuka, Kanagawa (JP); Ryuta Ueda, Kanagawa (JP); Yoshinori Hirano, Chiba (JP)

(73) Assignee: CANON KABUSHIKI KAISHA, Tokyo (JP)

(*) Notice: Subject to any disclaimer, the term of this patent is extended or adjusted under 35 U.S.C. 154(b) by 99 days.

(21) Appl. No.: 17/208,934

(22) Filed: Mar. 22, 2021

(65) Prior Publication Data
US 2021/0303917 A1 Sep. 30, 2021

(30) Foreign Application Priority Data
Mar. 26, 2020 (JP) ................................ 2020-055973

(51) Int. Cl.
| H04B 7/185 | (2006.01) |
| H04B 1/04 | (2006.01) |
| H04B 7/155 | (2006.01) |
| H04B 15/00 | (2006.01) |
| H04W 16/24 | (2009.01) |

(Continued)

(52) U.S. Cl.
CPC ............ *A61B 8/468* (2013.01); *A61B 8/4245* (2013.01); *A61B 8/463* (2013.01); *G06F 18/217* (2023.01); *G06F 18/2431* (2023.01); *G06F 18/285* (2023.01); *G06V 10/82* (2022.01); *G06V 40/103* (2022.01)

(58) Field of Classification Search
None
See application file for complete search history.

(56) References Cited

U.S. PATENT DOCUMENTS

| 4,870,422 A * | 9/1989 | Counselman, III ..... G01S 19/44 342/450 |
| 4,894,662 A * | 1/1990 | Counselman ........... G01S 19/37 342/450 |

(Continued)

FOREIGN PATENT DOCUMENTS

| CN | 1750527 A * | 3/2006 | |
| CN | 102668443 A * | 9/2012 | ....... H04L 25/03178 |

(Continued)

OTHER PUBLICATIONS

Milletari et al., V-Net: Fully Convolutional Neural Networks for Volumetric Medical Image Segmentation, Fourth International Conference on 3D Vision (Year: 2016).*

*Primary Examiner* — Mohammed Rachedine
(74) *Attorney, Agent, or Firm* — Canon U.S.A., Inc. IP Division

(57) ABSTRACT

An information processing apparatus includes an acquisition unit configured to acquire ultrasonic image data, an inference unit configured to infer a body mark corresponding to the ultrasonic image data acquired by the acquisition unit, and a display control unit configured to display the body mark inferred by the inference unit together with the ultrasonic image data.

17 Claims, 11 Drawing Sheets

(51) Int. Cl.
*A61B 8/00* (2006.01)
*G06F 18/20* (2023.01)
*G06F 18/21* (2023.01)
*G06F 18/2431* (2023.01)
*G06V 10/82* (2022.01)
*G06V 40/10* (2022.01)

(56) References Cited

U.S. PATENT DOCUMENTS

| | | | | |
|---|---|---|---|---|
| 9,687,204 | B2 * | 6/2017 | Mountney | A61B 8/4245 |
| 2003/0058182 | A1 * | 3/2003 | Bhattacharyya | H01Q 13/025 |
| | | | | 343/786 |
| 2005/0260948 | A1 * | 11/2005 | Regulinski | H04B 7/18563 |
| | | | | 455/12.1 |
| 2007/0239004 | A1 * | 10/2007 | Kakee | A61B 8/4245 |
| | | | | 600/437 |
| 2012/0027141 | A1 * | 2/2012 | Petrovic | H04N 21/426 |
| | | | | 375/350 |
| 2016/0218436 | A1 * | 7/2016 | Rao | H01Q 13/0241 |
| 2016/0278063 | A1 * | 9/2016 | Zhang | H04W 72/0473 |
| 2017/0345223 | A1 * | 11/2017 | Ishizu | G16H 50/20 |
| 2017/0353864 | A1 * | 12/2017 | Bull | H04W 16/10 |
| 2018/0034521 | A1 * | 2/2018 | Asakura | H04L 5/023 |
| 2018/0360427 | A1 * | 12/2018 | Nakano | G06T 7/74 |
| 2020/0294226 | A1 * | 9/2020 | Fujihara | G01S 15/8936 |
| 2022/0183662 | A1 * | 6/2022 | Ketonis | A61B 5/4523 |

FOREIGN PATENT DOCUMENTS

| | | | | | |
|---|---|---|---|---|---|
| CN | 109310400 | B | * | 6/2021 | A61B 8/0825 |
| JP | 2014008083 | A | | 1/2014 | |
| KR | 20160047921 | A | * | 5/2016 | |
| WO | WO-2006099443 | A1 | * | 9/2006 | H04B 7/1851 |
| WO | WO-2012137451 | A2 | * | 10/2012 | A61B 5/0037 |
| WO | WO-2014209003 | A1 | * | 12/2014 | A61B 8/4405 |

* cited by examiner

INFORMATION PROCESSING APPARATUS, INFORMATION PROCESSING METHOD, NON-TRANSITORY COMPUTER READABLE STORAGE MEDIUM, AND ULTRASONIC DIAGNOSIS APPARATUS

BACKGROUND

Field of the Disclosure

The present disclosure relates to an information processing apparatus that infers a body mark based on ultrasonic image data, an information processing method, a non-transitory computer readable storage medium, and an ultrasonic diagnosis apparatus.

Description of the Related Art

In tests using an ultrasonic diagnosis apparatus, a user scans a subject with a probe to capture an ultrasonic image. Japanese Patent Application Laid-Open No. 2014-008083 discusses, as a method for determining the correspondence between ultrasonic image data captured at a time of the test and a capturing position of the ultrasonic image, a technique by which a user sets a body mark indicating a diagnosis region in the ultrasonic image data and a probe mark indicating the position of the ultrasonic probe on the body mark.

SUMMARY

For each test, the user can grasp the correspondence between the ultrasonic image data and the capturing position of the ultrasonic image by setting the body mark and the probe mark for the test. On the other hand, setting the body mark and the probe mark at each test is troublesome for the user.

The present disclosure is directed to an information processing apparatus that is capable of inferring a body mark from the ultrasonic image data, which allows the user to grasp the correspondence relationship between the ultrasonic image data and the capturing position of the ultrasonic image while saving the user's time and effort.

According to an aspect of the present invention, an information processing apparatus includes an acquisition unit configured to acquire ultrasonic image data, an inference unit configured to infer a body mark corresponding to the ultrasonic image data acquired by the acquisition unit, and a display control unit configured to display the body mark inferred by the inference unit together with the ultrasonic image data.

Further features of the present disclosure will become apparent from the following description of exemplary embodiments with reference to the attached drawings.

DESCRIPTION OF THE EMBODIMENTS

Figure 1:
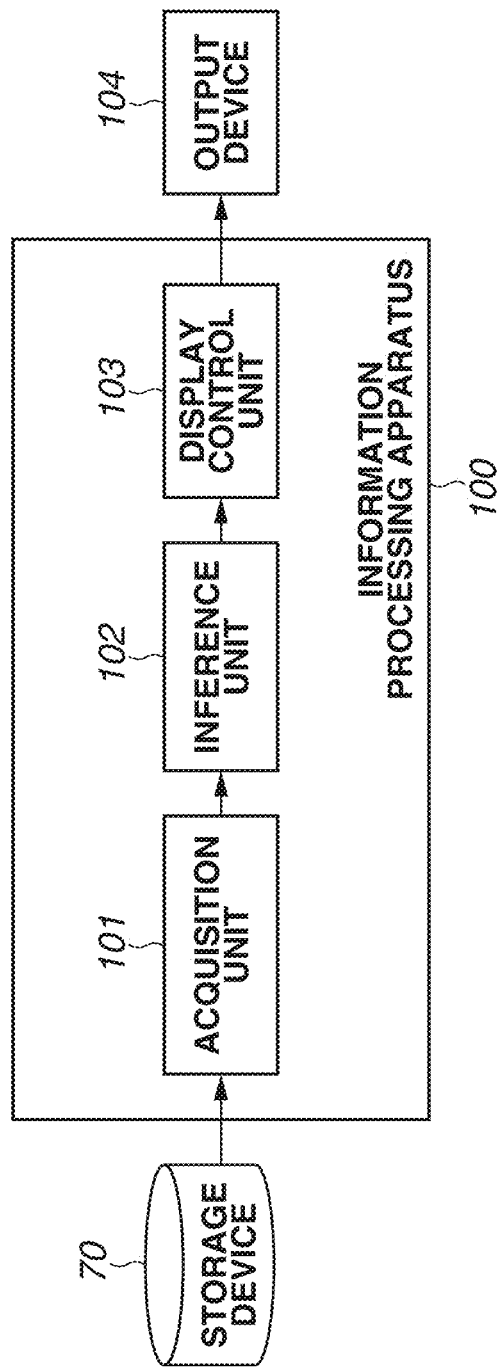
FIG. 1 is a block diagram illustrating a functional configuration of an information processing apparatus according to a first exemplary embodiment.

Hereinafter, exemplary embodiments of an information processing apparatus disclosed herein will be described with reference to the drawings. Identical constructional elements, members, and processing illustrated in the drawings are denoted with identical signs, and duplicated description thereof will be omitted as appropriate. Further, the present invention is not limited to the illustrated configurations.

In the following description, a functional configuration of a first exemplary embodiment will be described with reference to FIG. 1. An information processing apparatus 100 infers and displays a body mark and the position of a probe on the body mark with respect to ultrasonic image data captured using an ultrasonic diagnosis apparatus. Each of the components of the information processing apparatus 100 may be configured with an independent device or may be configured as a function of the ultrasonic diagnosis apparatus. A case where the information processing apparatus 100 is configured as a function of the ultrasonic diagnosis apparatus will be described below with reference to FIG. 5. This configuration or a part of this configuration may be implemented on a cloud via a network.

In the present exemplary embodiment, ultrasonic image data captured by a user is stored in a storage device 70. The information processing apparatus 100 acquires the ultrasonic image data from the storage device 70, infers a body mark and the position of a probe on the body mark based on the acquired ultrasonic image data, and causes an output device 104 to execute display processing. The output device 104 is a cathode-ray tube (CRT) monitor and a liquid crystal monitor, for example. Upon reception of a display instruction from the information processing apparatus 100, the output device 104 displays superimposed image data in which a probe mark is superimposed on the body mark. When the information processing apparatus 100 is provided as a function of the ultrasonic diagnosis apparatus, the output device 104 is a monitor mounted in the ultrasonic diagnosis apparatus. Hereinafter, the components of the information processing apparatus 100 will be described.

<Acquisition Unit 101>

An acquisition unit 101 in the information processing apparatus 100 acquires the target ultrasonic image data from the storage device 70. Upon acquisition of the target ultrasonic image data, the acquisition unit 101 transmits the target ultrasonic image data to an inference unit 102.

<Inference Unit 102>

The inference unit 102 in the information processing apparatus 100 infers a body mark and the position of a probe on the body mark with respect to the ultrasonic image data acquired and transmitted by the acquisition unit 101. The inference unit 102 infers the body mark and the position of the probe on the body mark, by using a classifier based on machine learning, for example.

The classifier based on machine learning in the inference unit 102 is a classifier that becomes capable of performing inference through learning processing based on supervisory data with pairs of correct labels and ground truth image data. Hereinafter, the leaning processing of the classifier constituting the inference unit 102, based on machine learning and the output of the classifier generated by the learning processing will be described.

The classifier based on machine learning constituting the inference unit 102 will be described with reference to Convolutional Neural Network (CNN) that is known as a model for a kind of deep learning among machine learning techniques. Instead of CNN, the classifier constituting the inference unit 102 may be configured by another machine learning technique such as a support vector machine (SVM). The machine learning technique constituting the inference unit 102 is used as appropriate to perform filtering processing for converting image data to a feature value, normalization processing, and the like.

The classifier based on CNN in the inference unit 102 performs learning processing based on supervisory data including pairs of correct labels and ground truth images. As a correct label, information indicating the type of a body mark and information associated with the position of a probe are set. The number of types of correct labels equals to, for example, the number obtained by multiplying the number of body marks by the number of positions of the probe. Each of the labels classified by the classifier is called a class and the inference by the classifier is called a class classification, for example. If the number of types of the correct labels is greater than the number of the ground truth images, the data may be extended to increase the absolute number of the data, or some of the correct labels may be integrated into one correct label.

As a ground truth images, ultrasonic image data of the subject captured in an image-capturing range at the position of the probe on the body mark corresponding to the correct label is used. The classifier based on machine learning is created by preparing a sufficient number of pieces of supervisory data including pairs of correct labels and ground truth images described above to learn the CNN model and executing learning processing. By using the classifier created by the learning processing, the inference unit 102 can infer the body mark and the position of the probe on the body mark with respect to the target ultrasonic image data that has been acquired by the acquisition unit 101. In other words, the classifier based on machine learning in the inference unit 102 is a classifier that has undergone the learning processing based on the supervisory data in which the information indicating the type of the body mark is set as the correct label and the ultrasonic image data captured in the image-capturing range corresponding to the correct label is set as the ground truth image.

In the output of the classifier in the inference unit 102, likelihood can be assigned to each of the correct labels by providing a softmax layer to the network layer constituting CNN. In other words, the inference unit 102 characteristically outputs the inference results as likelihood. The likelihood is the probability (reliability) of inference of a correct label, and the likelihoods of the class classifications made by the classifier add up to 1. The inference unit 102 outputs the results of the class classifications for the ultrasonic image data as likelihood and transmits the likelihood to a display control unit 103.

<Display Control Unit 103>

The display control unit 103 acquires the class and the likelihood assigned to the class as the inference results from the inference unit 102. The class is information in which the body mark and the position of the probe set as a correct label in the learning processing are associated with each other. Thus, the display control unit 103 acquires, from the inference unit 102, the body mark and the position of the probe on the body mark corresponding to the target ultrasonic image data as the class. The display control unit 103 generates superimposed image data in which a probe mark based on the probe position inferred by the inference unit 102 is superimposed on the acquired body mark, and causes the output device 104 to output the superimposed image data. In other words, the information processing apparatus 100 has the acquisition unit 101 that acquires ultrasonic image data, the inference unit 102 that infers a body mark and the position of a probe on the body mark for the ultrasonic image data, from the ultrasonic image data acquired by the acquisition unit 101, and the display control unit 103 that displays the body mark inferred by the inference unit 102 together with the ultrasonic image data.

The inference unit 102 further infers the position of the probe on the body mark from the ultrasonic image data acquired by the acquisition unit 101, and the display control unit 103 displays the superimposed image data in which the probe mark based on the inferred probe position is superimposed on the body mark inferred by the inference unit 102.

With the configuration described in the present exemplary embodiment, it is possible for the user to grasp the correspondence relationship between the ultrasonic image data and the capturing position of the ultrasonic image while saving the user's time and effort for setting the body mark and the probe mark.

<Hardware Configuration>

Figure 2:
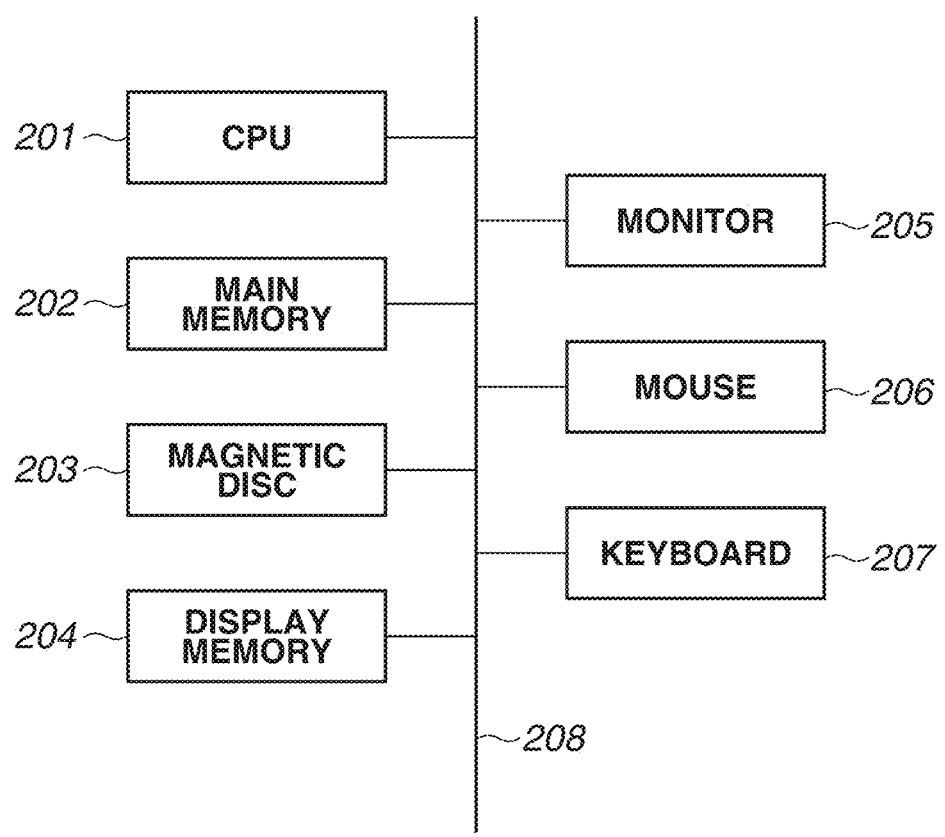
FIG. 2 is a block diagram illustrating an example of a hardware configuration of the information processing apparatus according to the first exemplary embodiment.

FIG. 2 is a block diagram illustrating an example of a hardware configuration of the information processing apparatus 100. A central processing unit (CPU) 201 mainly controls operations of the components. A main memory 202 stores control programs to be executed by the CPU 201, and provides a work area for the CPU 201 to execute the programs. A magnetic disc 203 stores programs for implementing various types of application software, including an operating system (OS), device drivers for peripheral devices, and programs for performing processing described below. The CPU 201 executes the programs stored in the main memory 202, the magnetic disc 203, or the like to implement the functions (software) of the information processing apparatus 100 illustrated in FIG. 1 and the processing in the flowcharts described below.

A display memory 204 temporarily stores display data. A monitor 205 is a CRT monitor or a liquid crystal monitor, for example, which displays image data, text data, and the like based on the data transmitted from the display memory 204. The monitor 205 may operate as the output device 104 in the information processing apparatus 100. A mouse 206 and a keyboard 207 are used by the user to perform pointing input and character input, respectively. The components described above are communicably connected to each other via a common bus 208.

The CPU 201 corresponds to an example of a processor. The information processing apparatus 100 may have at least any one of a graphics processing unit (GPU) and a field-programmable gate array (FPGA) in addition to the CPU 201. Alternatively, the information processing apparatus 100 may have at least any one of a GPU and an FPGA instead of the CPU 201. The main memory 202 and the magnetic disc 203 each correspond to an example of memory.

<Processing Procedure>

Figure 3:
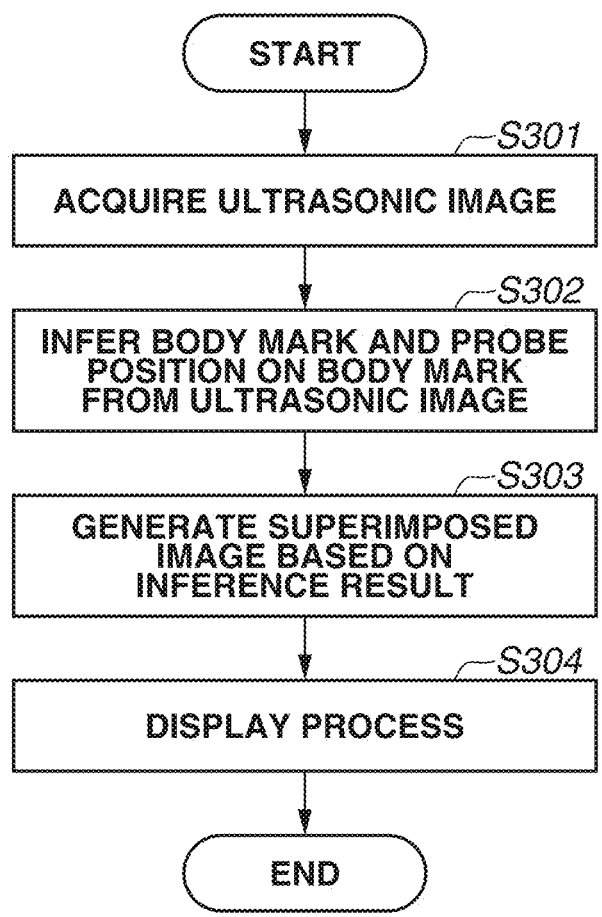
FIG. 3 is a flowchart illustrating a procedure performed by the information processing apparatus according to the first exemplary embodiment.

Next, a processing procedure of the information processing apparatus 100 in the present exemplary embodiment will be described with reference to the flowchart in FIG. 3.

First, in step S301, the acquisition unit 101 acquires the processing target ultrasonic image data from the storage device 70. Upon acquisition of the ultrasonic image data, the acquisition unit 101 transmits the ultrasonic image data to the inference unit 102.

In step S302, the inference unit 102 infers a body mark and the position of a probe on the body mark with respect to the ultrasonic image data transmitted from the acquisition unit 101. The inference unit 102 performs the inference using a classifier based on machine learning. The classifier in the inference unit 102 is a classifier that has learned by the learning processing described above, and outputs, as output results, the body mark and the position of the probe on the body mark (class) for the input ultrasonic image data and its likelihood. The inference unit 102 transmits the output results provided by the classifier to the display control unit 103.

In step S303, the display control unit 103 acquires the body mark and the position of the probe on the body mark, and the likelihood of the classification made by the classifier. The display control unit 103 further generates the superimposed image data in which the probe mark is superimposed on the body mark based on the position of the probe on the body mark. The display control unit 103 transmits the generated superimposed image data to the output device 104. Depending on the likelihood provided by the classifier, the display control unit 103 may transmit, to the output device 104, a display screen for allowing the user to input an instruction, without displaying the body mark.

In step S304, the output device 104 displays the superimposed image data transmitted from the display control unit 103. This allows the user to grasp the correspondence relationship between the ultrasonic image data and the capturing position of the ultrasonic image data while saving the user's time and effort for setting the body mark and the probe mark.

An example of a display screen including the superimposed image data to be output to the output device 104 by the display control unit 103 will be described with reference to FIG. 4.

Figure 4:
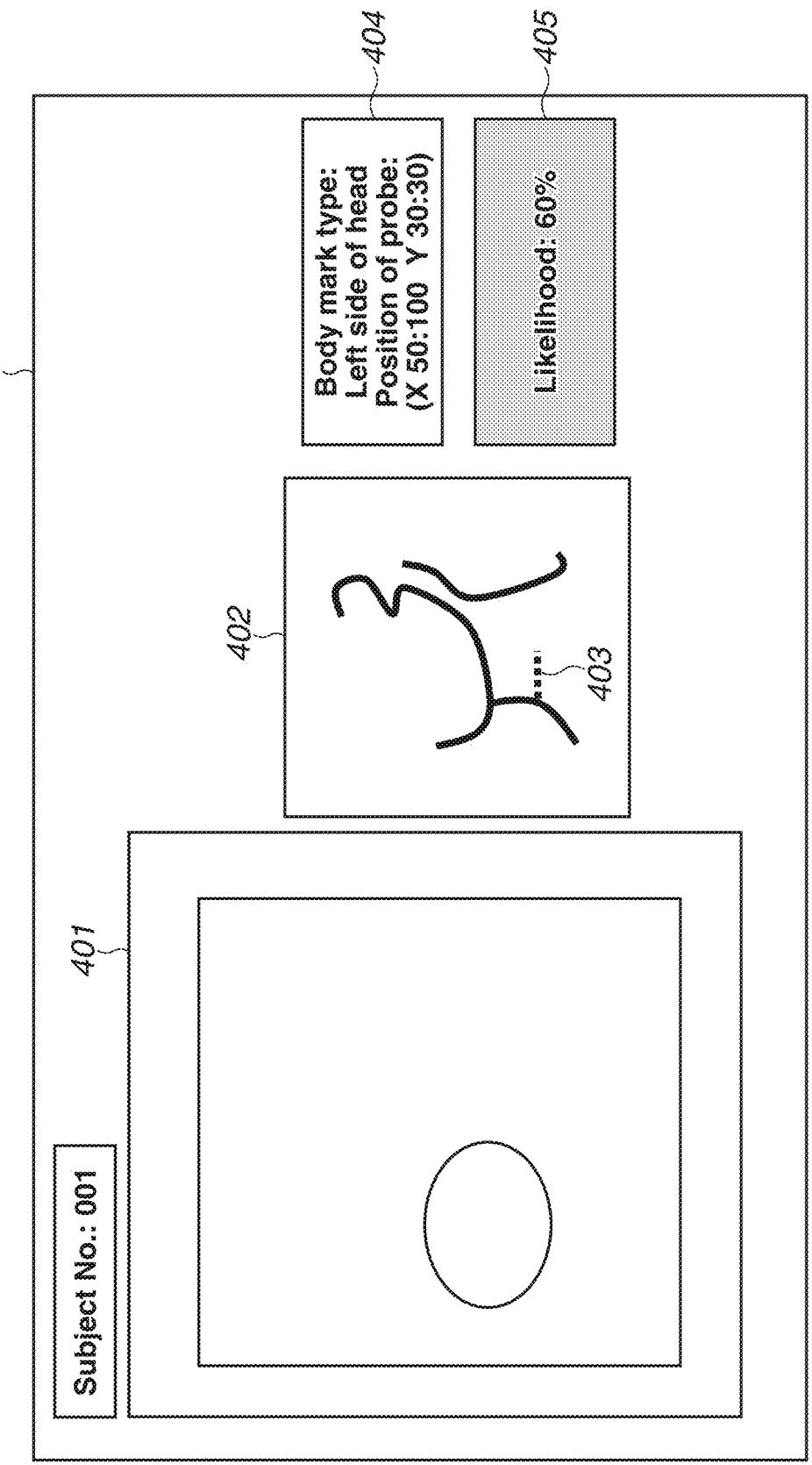
FIG. 4 is a diagram illustrating an example of a display screen according to the first exemplary embodiment.

FIG. 4 illustrates an example of a display screen to be subjected to display processing by the display control unit 103. A display screen 400 illustrated in FIG. 4 has an ultrasonic image data display field 401 where ultrasonic image data captured for a test is displayed. The display screen 400 further includes a superimposed image data display field 402 where superimposed image data is displayed near the ultrasonic image data. In the superimposed image data display field 402, a probe mark 403 based on information indicating a probe position on a body mark inferred by the inference unit 102 is superimposed on the body mark. The display screen 400 further includes an inference result display field 404 where results of inference by the inference unit 102 is displayed and a likelihood display field 405 in which the likelihood of the inference by the inference unit 102 is indicated. In other words, the display control unit 103 displays the superimposed image data and the likelihood in association with each other. In the inference result display field 404, information indicating the type of the body mark and coordinate information indicating, for example, a start point and an end point in XY coordinates are described as the position of the probe. The position of the probe may be represented by the name of the part specified by the user, not by the coordinate information. In the likelihood display field 405, a value indicating the likelihood provided by the inference unit 102 is displayed in percentage. This display screen is an example, and if the likelihood is higher than a threshold, for example, the likelihood may not be displayed in the display screen, whereas if the likelihood is lower than the threshold, an indication allowing the user to set a body mark or a probe mark may be displayed in the display screen.

Figure 5:
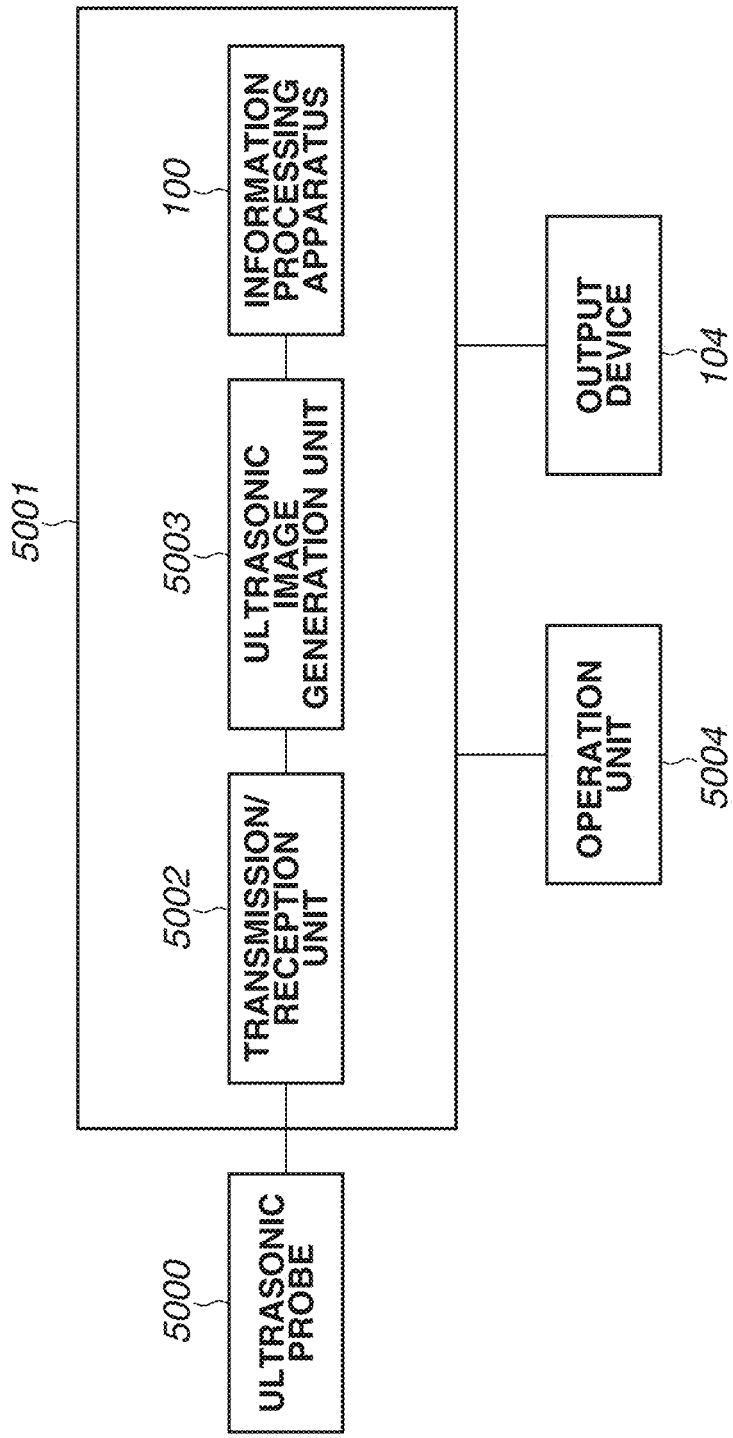
FIG. 5 is a block diagram illustrating a functional configuration of an ultrasonic diagnosis apparatus.

A configuration of the information processing apparatus 100 that operates as a function of an ultrasonic diagnosis apparatus will be described with reference to FIG. 5. The ultrasonic diagnosis apparatus includes an ultrasonic prove 5000 that is brought into contact with a subject to transmit and receive ultrasonic waves, an apparatus body 5001 that processes an ultrasonic signal received by the ultrasonic prove 5000 to generate ultrasonic image data and performs various measurements, an operation unit 5004 for operating the apparatus body 5001, and an output device 104 such as a monitor that outputs the ultrasonic image data, measurement results, and the like. The information processing apparatus 100 also operates as one of components of the apparatus body 5001 in the ultrasonic diagnosis apparatus.

The ultrasonic prove 5000 is connected to the apparatus body 5001. The ultrasonic prove 5000 has a plurality of vibrators and is capable of generating an ultrasonic wave by driving the plurality of vibrators. The ultrasonic prove 5000 receives the reflected wave from the subject and converts the received reflected wave into an electric signal. The converted electric signal is transferred to the apparatus body 5001.

The ultrasonic prove 5000 includes an acoustic matching layer provided on the front side (subject side) of the plurality of vibrators to match the acoustic impedance of the plurality of vibrators to the acoustic impedance of the subject, and a backing material provided on the rear side of the plurality of vibrators and prevents propagation of an ultrasonic wave from the plurality of vibrators to the rear side.

The ultrasonic prove 5000 is removably connected to the apparatus body 5001. The types of the ultrasonic prove 5000 include a linear type, a sector type, a convex type, a radial type, and a three-dimensional scanning type. The operator can select a type of the ultrasonic prove 5000 depending on the purpose of image capturing.

The apparatus body 5001 has a transmission/reception unit 5002 that transmits and receives an ultrasonic wave to and from the ultrasonic prove 5000, an ultrasonic image data generation unit 5003 that uses the ultrasonic signal received by the transmission/reception unit 5002 to generate ultrasonic image data, and the information processing apparatus 100 that infers a body mark from the generated ultrasonic image data.

The transmission/reception unit 5002 controls transmission and reception of an ultrasonic wave by the ultrasonic prove 5000. The transmission/reception unit 5002 has a pulse generation unit, a transmission delay circuit, and the like, and supplies a drive signal to the ultrasonic prove 5000. The pulse generation unit repeatedly generates a rate pulse with a predetermined pulse repetition frequency (PRF). The transmission delay circuit converges the ultrasonic wave generated from the ultrasonic prove 5000 and provides a delay time for determining transmission directional characteristics to the rate pulse generated by the pulse generation unit. The transmission delay circuit can control the transmission directions of the ultrasonic waves transmitted from the vibrators by changing the delay time to be provided to the rate pulse.

The transmission/reception unit 5002 also has an amplifier, an analog to digital (A/D) conversion unit, a reception-signal delay circuit, an addition unit, and the like. The transmission/reception unit 5002 performs various kinds of processing on the reflected wave signal received by the ultrasonic prove 5000 to generate an ultrasonic signal. The amplifier amplifies the reflected wave signal for each channel to perform gain correction processing. The A/D conversion unit A/D converts the gain-corrected reflected wave signal. The reception-signal delay circuit provides a delay time for determining signal-reception directional characteristics to the digital data. The addition unit performs addition processing on the reflected wave signal to which the delay time has been provided by the reception-signal delay circuit. The addition processing by the addition unit emphasizes the reflection components coming from the direction of the signal-reception directional characteristics of the reflected wave signal.

When the subject is to be two-dimensionally scanned, the transmission/reception unit 5002 transmits a two-dimensional ultrasonic wave from the ultrasonic prove 5000. Then, the transmission/reception unit 5002 generates a two-dimensional ultrasonic signal from the two-dimensional reflected wave signal received by the ultrasonic prove 5000. When the subject is to be three-dimensionally scanned, the transmission/reception unit 5002 transmits a three-dimensional ultrasonic wave from the ultrasonic prove 5000. Then, the transmission/reception unit 5002 generates a three-dimensional ultrasonic signal from the three-dimensional reflected wave signal received by the ultrasonic prove 5000.

The ultrasonic image data generation unit 5003 performs various kinds of signal processing on the ultrasonic signal output from the transmission/reception unit 5002 to generate ultrasonic image data. The ultrasonic image data generation unit 5003 performs signal processing such as wave detection and logarithmic compression on the ultrasonic signal to generate ultrasonic image data (B-mode image data) in which the signal intensity is represented by luminance.

The information processing apparatus 100 executes the processing described above on the ultrasonic image data generated by the ultrasonic image data generation unit 5003.

The operation unit 5004 has a mouse, a keyboard, buttons, panel switches, a touch command screen, a foot switch, a track ball, a joystick, and the like. The operation unit 5004 accepts various instructions from the operator of the ultrasonic diagnosis apparatus and transfers the accepted various instructions to the apparatus body 5001.

The output device 104 displays GUIs for the operator of the ultrasonic diagnosis apparatus to input various instructions using the operation unit 5004, displays ultrasonic image data generated by the apparatus body 5001, or displays a display screen generated by the information processing apparatus 100.

Since the information processing apparatus 100 operates as one of the components of the ultrasonic diagnosis apparatus, the user can use the ultrasonic diagnosis apparatus to perform the processing on the information processing apparatus 100 and display and check the processing results. This allows the user to grasp the correspondence relationship between the ultrasonic image data and the capturing position of the ultrasonic image while saving the user's time and effort for setting the body mark and the probe mark in the ultrasonic diagnosis apparatus.

Figure 6:
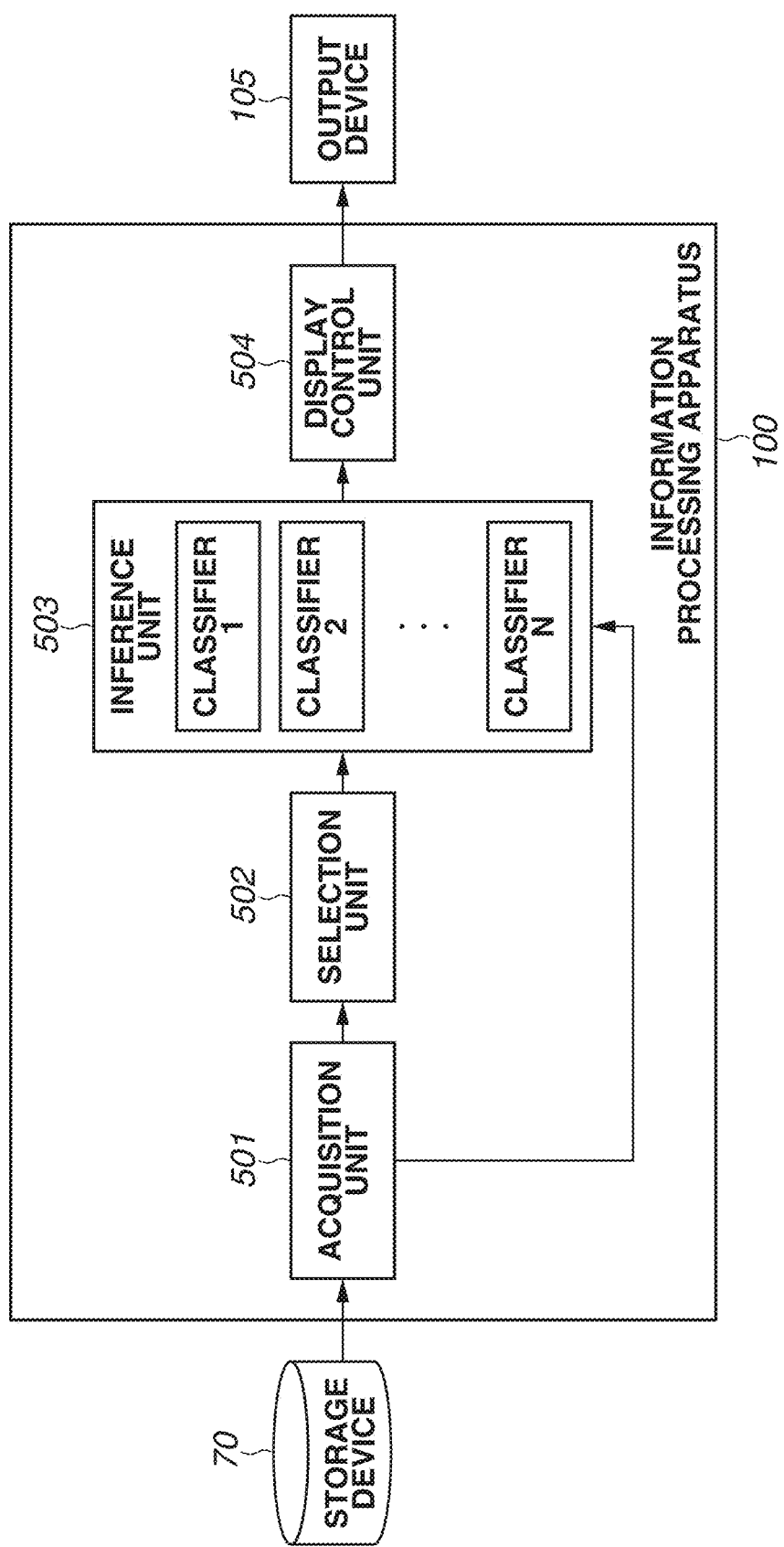
FIG. 6 is a block diagram illustrating a functional configuration of an information processing apparatus according to a second exemplary embodiment.

In the first exemplary embodiment, the description is given of a case where the information acquired by the acquisition unit 101 is ultrasonic image data, and the process is performed on the ultrasonic image data. In a second exemplary embodiment to be described with reference to FIG. 6, an acquisition unit 501 acquires not only ultrasonic image data but also information on the type of an ultrasonic probe and information input by a user. In the present exemplary embodiment, an inference unit 503 includes a plurality of classifiers. In other words, the inference unit 503 characteristically includes the plurality of classifiers. In addition, a selection unit 502 is provided to select a classifier to infer a body mark and the position of a probe on the body mark, from among the plurality of classifiers, based on the information acquired by the acquisition unit 501. Hereinafter, components of an information processing apparatus 100 according to the second exemplary embodiment will be described.

<Acquisition Unit 501>

The acquisition unit 501 acquires, from a storage device 70, the ultrasonic image data and the information on the type of the ultrasonic probe that was used to capture the ultrasonic image data. Examples of types of the ultrasonic probe include a convex type, a sector type, and a linear type. The acquisition unit 501 may accept inputs of the information on the ultrasonic probe and a diagnosis region from the user via the mouse 206 or the keyboard 207, for example. The acquisition unit 501 transmits the acquired information on the ultrasonic probe and information on the diagnosis region to the selection unit 502. The acquisition unit 501 also transmits the ultrasonic image data to the inference unit 503.

<Selection Unit 502>

When the information transmitted from the acquisition unit 501 is the information indicating the type of the ultrasonic probe, the selection unit 502 acquires candidates for the diagnosis region by comparing the information with a table in which the candidates for the diagnosis region are stored for each type of ultrasonic probe. On the other hand, when the acquired information is the information on the diagnosis region, the selection unit 502 acquires the information on the diagnosis region as the information on diagnosis region candidates. Based on the acquired diagnosis region candidates, the selection unit 502 selects a classifier from the inference unit 503 to perform inference with respect to the ultrasonic image data acquired by the acquisition unit 501.

<Inference Unit 503>

The inference unit 503 infers a body mark and the position of a probe on the body mark from the ultrasonic image data, using the classifier selected by the selection unit 502. The plurality of classifiers constituting the inference unit 503 is, for example, classifiers that have learned supervisory data for each diagnosis region. The learning processing for each diagnosis region can generate a classifier suitable for classifying an abdominal region, for example, by learning supervisory data in which information of the body mark corresponding to the abdominal region and the position of a probe on the body mark that are associated with each other is set as a correct label and ultrasonic image data of a diagnosis region captured corresponding to the position of the probe on the body mark corresponding to the abdominal region is set as a ground truth image. It is noted that classifiers having undergone similar learning processing are provided for other diagnosis regions. With the plurality of classifiers respectively corresponding to the diagnosis regions, it can be expected, for example, to simplify the model structure of CNN, decrease the number of pieces of supervisory data, and reduce the processing time for learning and inference. Narrowing down the diagnostic targets in advance achieves a certain degree of accuracy even if image data in different diagnosis regions have similar image data feature values. The inference unit 503 transmits the information indicating the body mark inferred by using the classifier and the probe position on the body mark to a display control unit 504.

<Display Control Unit 504>

The display control unit 504 causes an output device 105 to display the information on the classifier having performed the inference, in addition to performing the same processing as that performed by the display control unit 103 in the first exemplary embodiment described above. A display screen caused to be displayed by the display control unit 504 will be described below. As a whole, in the information processing apparatus 100, the acquisition unit 501 further acquires the type of the probe. The information processing apparatus 100 further includes the selection unit 502 that selects the classifier to perform inference from among the plurality of classifiers constituting the inference unit 503 in accordance with the acquired type of the probe. The inference unit 503 characteristically uses the classifier selected by the selection unit 502 to infer, from the ultrasonic image data, a body mark corresponding to the ultrasonic image data and the position of the probe on the body mark.

Figure 7:
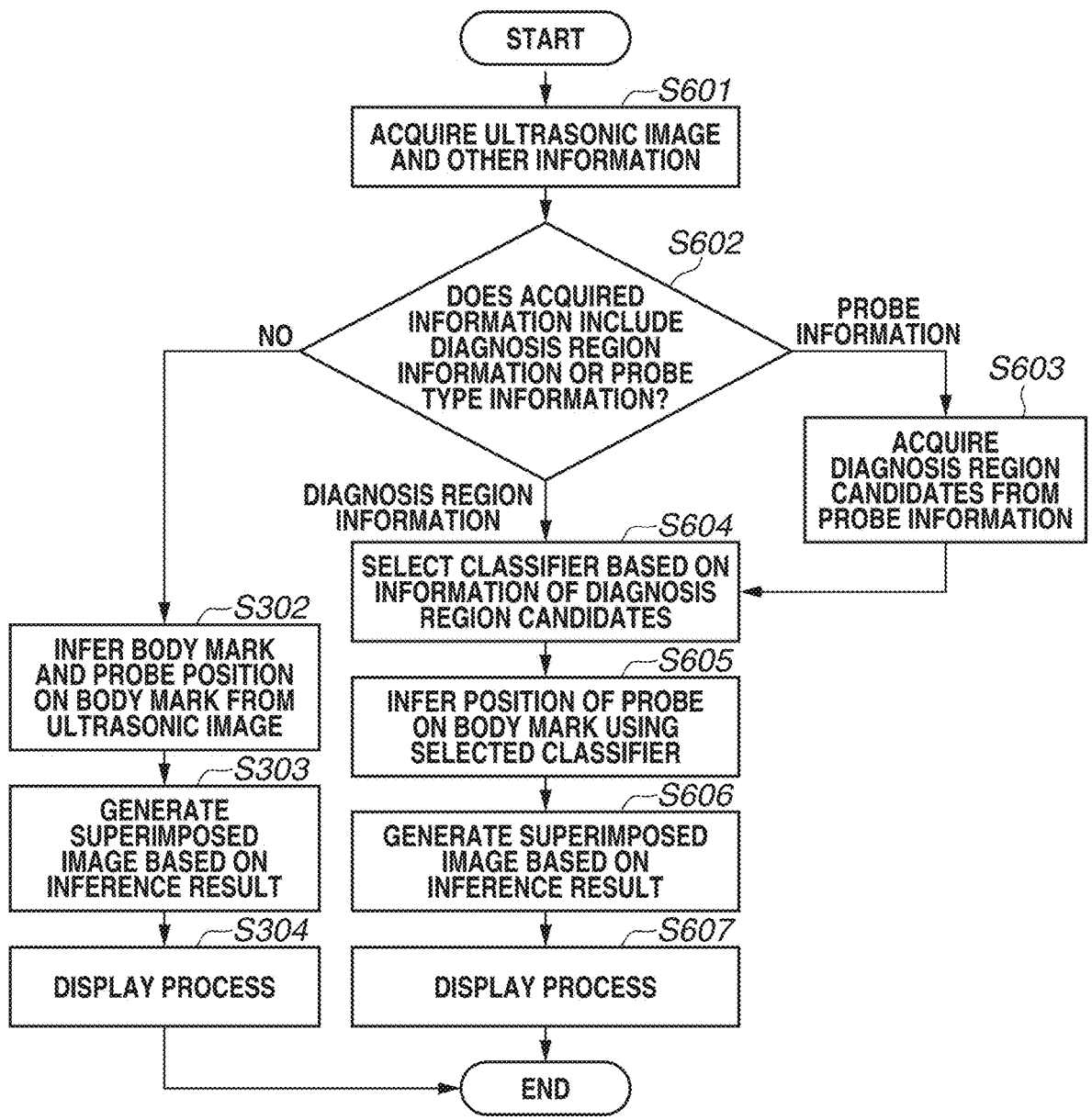
FIG. 7 is a flowchart illustrating a procedure performed by the information processing apparatus according to the second exemplary embodiment.

The processing by the information processing apparatus 100 according to the second exemplary embodiment will be described with reference to the flowchart in FIG. 7. In step S601, the acquisition unit 501 acquires ultrasonic image data and other information from the storage device 70. The other information refers to information indicating the type of the ultrasonic probe that was used to capture the ultrasonic image or information indicating the diagnosis region input by the user. The acquisition unit 501 transmits the acquired ultrasonic image data to the inference unit 503, and transmits the other information to the selection unit 502.

In step S602, the selection unit 502 determines whether the acquired other information includes the information indicating the diagnosis region or the information indicating the type of the probe. When the other information transmitted from the acquisition unit 501 does not include the information indicating the diagnosis region or the information indicating the type of the probe, the selection unit 502 performs inference and displays inference results in the procedure described above in the first exemplary embodiment. When it is determined in step S602 that the information transmitted by the acquisition unit 501 includes the information indicating the type of the probe (the other information includes the information indicating the type of the probe), the processing proceeds to step S603. In step S603, the selection unit 502 acquires candidates for the diagnosis region by comparing the information with the table in which the candidates for the diagnosis region are stored for each type of ultrasonic probe, and then the processing proceeds to step S604. On the other hand, when it is determined in step S602 that the other information transmitted from the acquisition unit 501 includes the information indicating the diagnosis region (the other information includes the information indicating the diagnosis region), the selection unit 502 acquires the candidates for the diagnosis region from the information on the diagnosis region, and the processing proceeds to step S604. In step S604, based on the acquired region candidates, the selection unit 502 selects a classifier to infer the ultrasonic image data from among the plurality of classifiers constituting the inference unit 503. When the selection unit 502 selects the classifier to perform inference on the ultrasonic image data, the processing proceeds to step S605. In step S605, the inference unit 503 uses the classifier selected by the selection unit 502 to infer the ultrasonic image data transmitted from the acquisition unit 501. The classifier infers the body mark and the position of the probe on the body mark as described above in the first exemplary embodiment. The inference unit 503 transmits information on the classifier having performed the inference, together with the inference results, to the display control unit 504.

In step 606, the display control unit 504 acquires the inference results and the information on the classifier having performed the inference, from the inference unit 503. As in the first exemplary embodiment, the display control unit 504 generates superimposed image data in which a probe mark based on the position of the probe on the body mark is superimposed on the body mark. In step S607, the display control unit 504 causes the output device 105 to display the generated superimposed image data and the information including the information indicating the inferred classification in a display screen.

Figure 8:
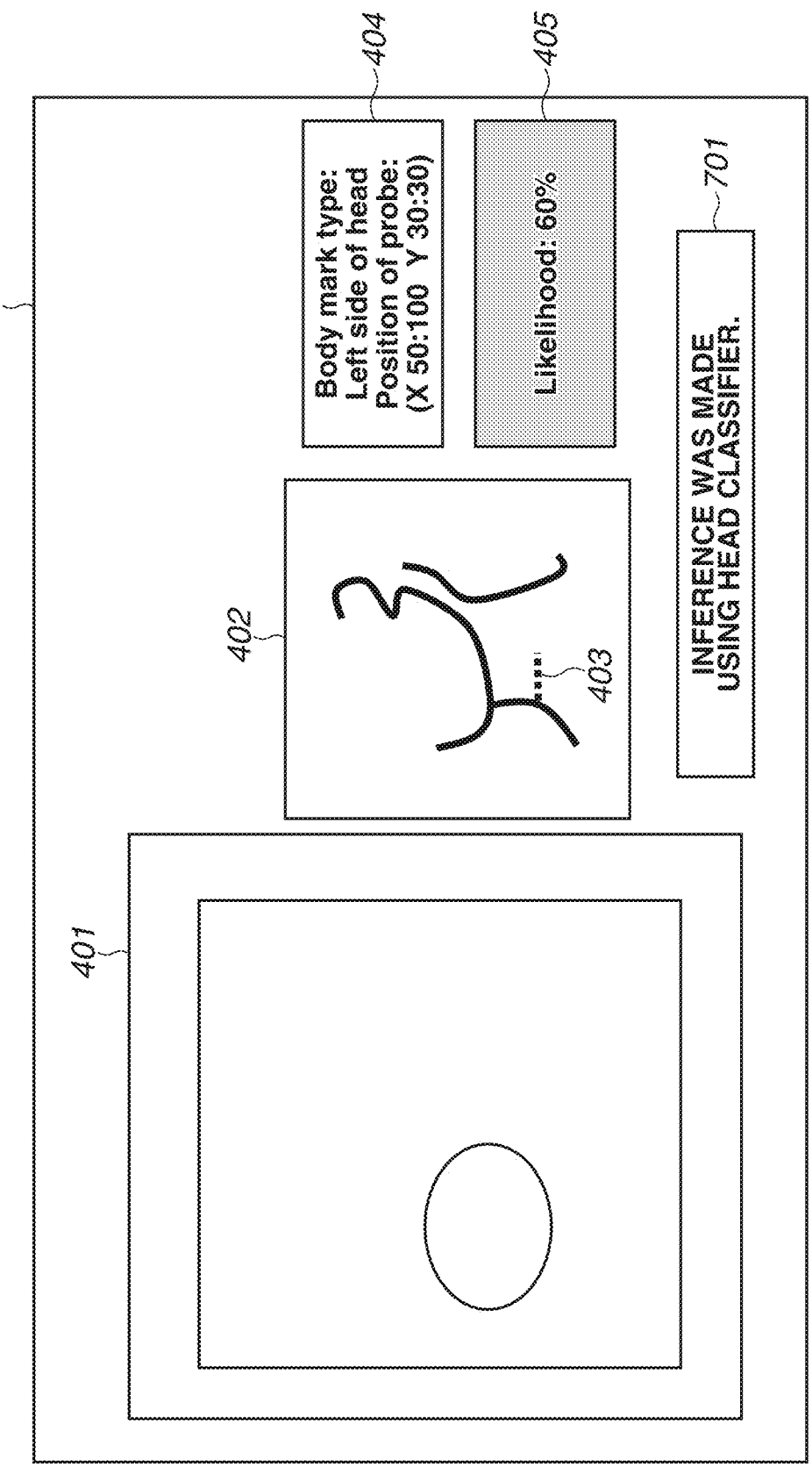
FIG. 8 is a diagram illustrating an example of a display screen according to the second exemplary embodiment.

Hereinafter, a display screen 700 caused to be displayed by the display control unit 504 will be described with reference to FIG. 8. In the description, only the differences from the display screen 400 illustrated in FIG. 4 will be described. The display screen 700 includes a classifier information display field 701 in which the information on the classifier having performed inference is displayed, in addition to the display fields in the display screen 400 of FIG. 4.

With the present exemplary embodiment, the user can grasp the correspondence relationship between the ultrasonic image data and the capturing position of the ultrasonic image data while saving the time and effort for setting the body mark and the probe mark. With the plurality of classifiers respectively corresponding to the diagnosis regions, it can be expected, for example, to simplify the model structure of CNN, decrease the number of pieces of supervisory data, and reduce the processing time for learning and inference. In addition, acquiring the information on the diagnosis region and the information indicating the type of the probe and narrowing down the diagnostic objectives in advance achieves a certain degree of accuracy and increases the accuracy of the contents to be displayed, even if image data in different diagnosis regions have similar image data feature values.

Variation Example

Now, as a variation example, a case where an information processing apparatus 100 has a determination unit 801 that determines results of inference inferred by an inference unit 102 will be described. This variation example is applicable to both the first exemplary embodiment and the second exemplary embodiment, and the configuration of the variation example may be combined with the exemplary embodiments described above.

Figure 9:
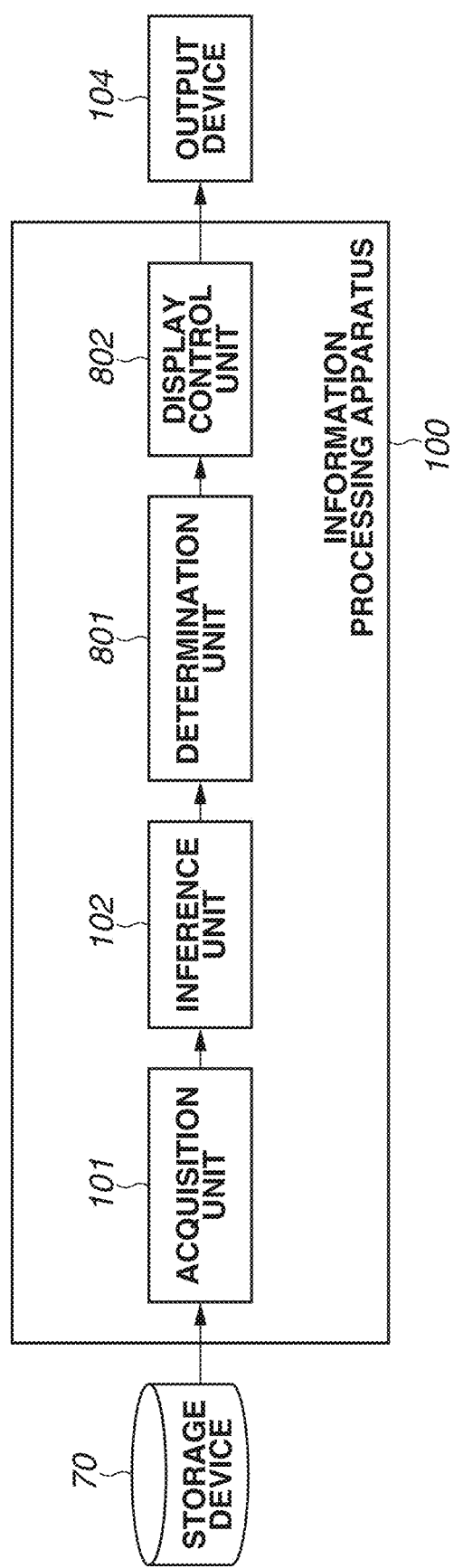
FIG. 9 is a block diagram illustrating a functional configuration of an information processing apparatus according to a variation example.

The variation example will be described with reference to FIG. 9, which is a block diagram illustrating a functional configuration of the variation example. The information processing apparatus 100 according to the variation example has an acquisition unit 101 that acquires ultrasonic image data, an inference unit 102 that infers a body mark and the position of a probe mark from the ultrasonic image data, and the determination unit 801 that determines results of inference by the inference unit 102. The information processing apparatus 100 further has a display control unit 802 that provides display based on results of determination by the determination unit 801. Hereinafter, components different from those in the exemplary embodiments described above will be described, and description of duplicated components will be omitted as appropriate.

<Determination Unit 801>

The determination unit 801 acquires the results of inference classified by the classifier in the inference unit 102. The determination unit 801 compares the likelihood of class classification in the acquired inference results with a predetermined reference. When the likelihood satisfies the predetermined reference, the determination unit 801 displays a display screen as described above as the display screen example in the first exemplary embodiment or the second exemplary embodiment. On the other hand, when the likelihood acquired by the inference unit 102 does not satisfy the predetermined reference, the determination unit 801 transmits a plurality of classes constituting the inference results and the likelihoods respectively corresponding to the classes to the display control unit 802. The predetermined reference is a threshold value for the likelihood corresponding to the class, for example. The likelihood corresponding to the class is a value expressing, with a probability, a reliability of the classification by the classifier constituting the inference unit 102. For example, as the likelihood corresponding to the class is low, the reliability is low too. Therefore, providing the threshold for the likelihoods respectively corresponding to the classes allows for acquisition of the inference results from which the classes with low reliability are omitted. As the predetermined reference used by the determination unit 801 for determination, the likelihoods respectively corresponding to classes between the plurality of classes constituting the inference results may be compared with each other. As a result of the classification by the classifier, when the difference between the likelihoods respectively corresponding to the classes between the plurality of classes is small, it is difficult for the classifier to classify the ultrasonic image data to be inferred. Thus, the determination unit 801 determines whether at least one of the likelihood corresponding to the class constituting the inference results and the difference between the likelihoods respectively corresponding to the plurality of classes satisfies the predetermined reference.

A predetermined reference as exemplified here is set, and the determination unit 801 compares the likelihood corresponding to the class as the results of the inference by the inference unit 102 with the predetermined reference. When the likelihood corresponding to the class does not satisfy the predetermined reference, the determination unit 801 transmits the information indicating the class (the body mark and the position of the probe mark) and the likelihood corresponding to the class to the display control unit 802.

<Display Control Unit 802>

The display control unit 802 acquires the class and the likelihood corresponding to the class transmitted by the determination unit 801, and generates a display screen to be displayed on the output device 104. An example of a display screen subjected to display processing by the display control unit 802 will be described below. Here, the display control unit 802 generates superimposed image data from the plurality of classes constituting the inference results determined as not satisfying the predetermined reference by the determination unit 801 and the likelihoods respectively corresponding to the classes, and performs display processing on the superimposed image data. Thus, the display control unit 802 changes the number of pieces of display image data to be displayed based on the results of determination by the determination unit 801. In other words, the display control unit 802 changes the number of the superimposed image unit 802 to be displayed depending on the determination results. Besides the number of pieces of superimposed image data, the display control unit 802 may change display size, color, the presence or absence of blinking, or the like, in accordance with the likelihoods. For example, the display control unit 802 generates superimposed image data for the classes with the similar likelihoods, and causes the output device 104 to display the data in the display screen.

With this configuration, even if the results of inference by the classifier constituting the inference unit 102 do not satisfy the predetermined reference, it is possible to present candidates for superimposed image data for the user to grasp the correspondence relationship between the ultrasonic image data and the capturing position of the ultrasonic image. The user also can determine the superimposed image data for grasping the capturing position from among the candidates by selecting the superimposed image data indicating the capturing position from among the candidates by using the mouse 206 or the keyboard 207.

Figure 10:
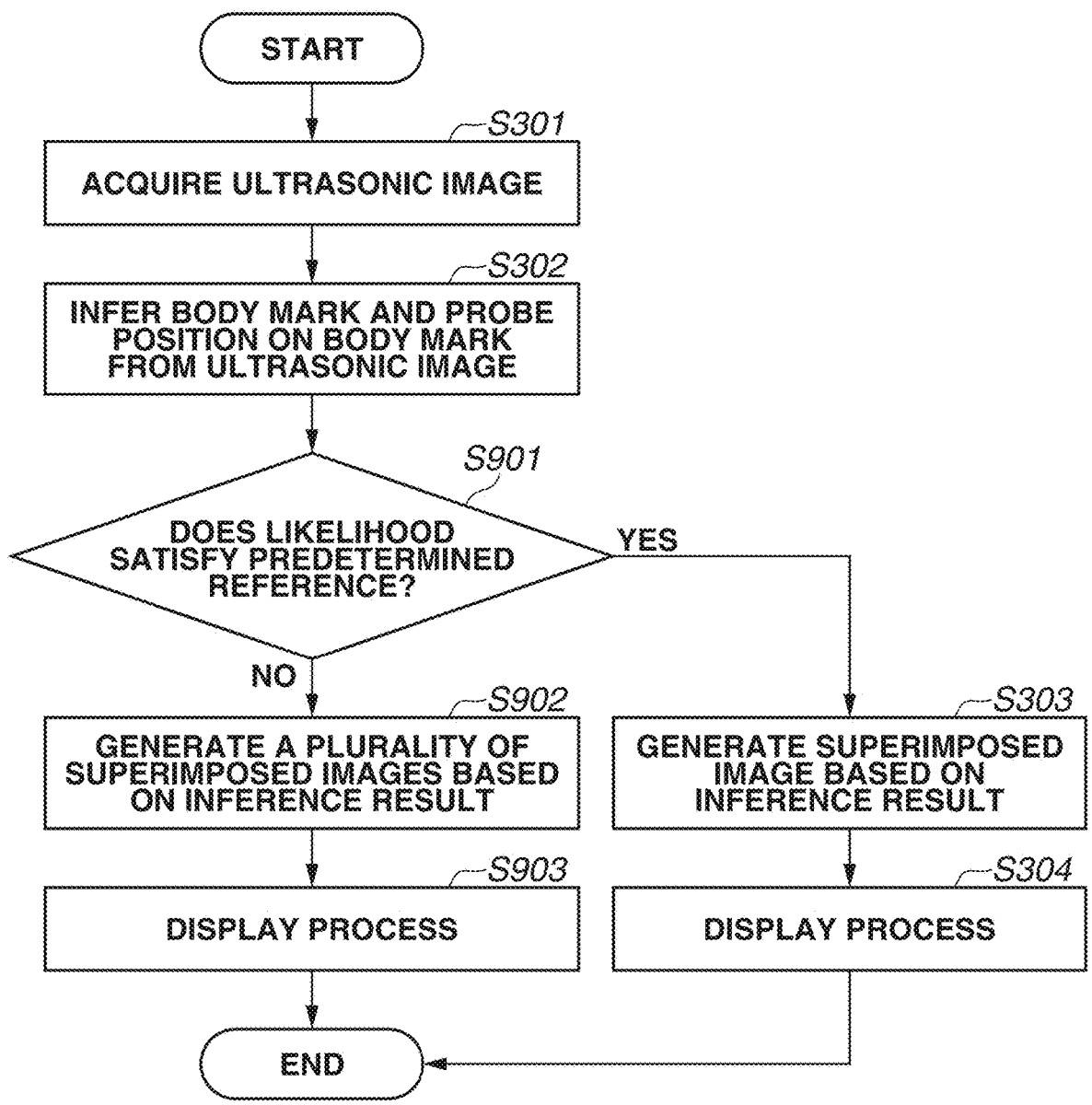
FIG. 10 is a flowchart illustrating a procedure performed by the information processing apparatus according to the variation example.

Hereinafter, the processing performed by the information processing apparatus 100 of the variation example will be described with reference to the flowchart of FIG. 10. In step S901, the determination unit 801 acquires a class and a likelihood corresponding to the class as inference results from the inference unit 102. The class corresponds to a body mark and the position of a probe inferred by the inference unit 102. In step S901, the determination unit 801 compares the likelihood corresponding to the acquired class with a predetermined reference. When the likelihood in the inference results satisfies the predetermined reference (YES in step S901), the processing proceeds to step S303. The predetermined reference is a threshold or a difference between likelihoods respectively corresponding to classes as described above. When the likelihood corresponding to the class does not satisfy the predetermined reference (NO in step S901), the determination unit 801 transmits the information indicating the classes and the likelihoods respectively corresponding to the classes to the display control unit 802.

In step S902, the display control unit 802 acquires the classes and the likelihoods respectively corresponding to the classes from the determination unit 801. The display control unit 802 generates pieces of superimposed image data respectively corresponding to the classes acquired from the determination unit 801 and causes the superimposed image data to be displayed as a display screen. The display control unit 802 determines the display screen to be displayed on the output device 104 based on the results of determination by the determination unit 801. An example of a display screen displayed by the display control unit 802 will be described with reference to FIG. 11.

Figure 11:
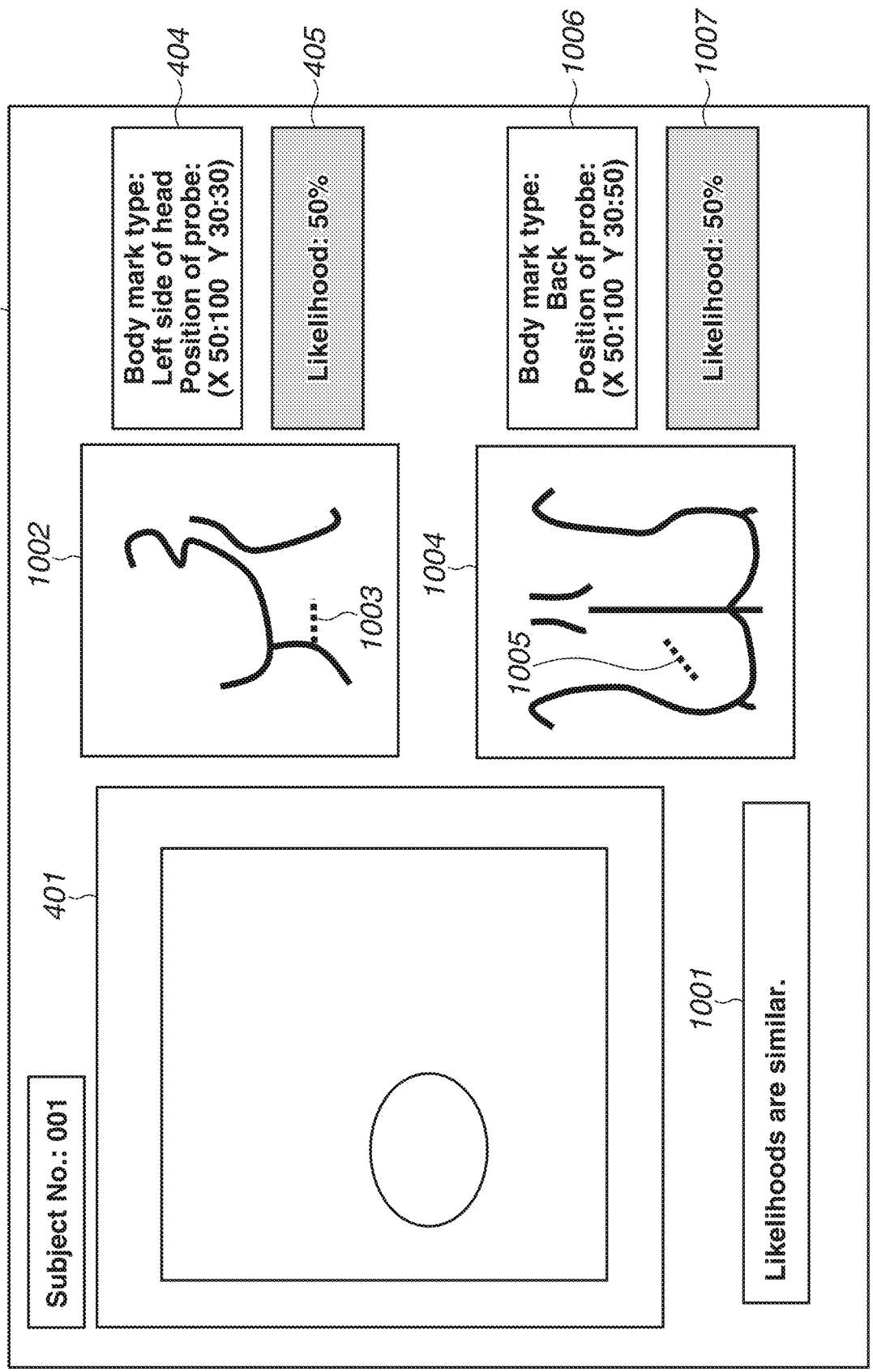
FIG. 11 is a diagram illustrating an example of a display screen according to the variation example.

FIG. 11 illustrates an example of a display screen 1000 displayed on the output device 104 by the display control unit 802. The display screen 1000 includes superimposed image data display fields 1002 and 1004 in which pieces of superimposed image data respectively corresponding to the acquired classes are displayed. The display screen 1000 also includes a probe mark 1003 and a probe mark 1005 corresponding to the superimposed image data. In the display screen 1000, the classes (the body marks indicating the left side of the head and the back, and the positions of the probe marks) with a likelihood of 50% and a difference in between not satisfying the predetermined reference are acquired and displayed. Thus, the inference results corresponding to the body mark of the back and the position of the probe mark are displayed in an inference result display field 1006, and the likelihood of the inference is displayed in a likelihood display field 1007. With this configuration, even if the results of inference by the classifier constituting the inference unit 102 do not satisfy the predetermined reference, it is possible to present candidates for superimposed image data from which the user can grasp the correspondence relationship between the ultrasonic image data and the capturing position of the ultrasonic image. The user also can determine the superimposed image data for grasping the capturing position from among the candidates by selecting the superimposed image data indicating the capturing position from among the candidates by using the mouse 206 or the keyboard 207.

Other Embodiments

The present invention can be implemented by executing the processing described below. Specifically, the processing is performed by supplying software (programs) for implementing the functions of the exemplary embodiments descried above to a system or an apparatus via a network or any of various computer readable storage media and reading and executing the programs by a computer (or a CPU or MPU) in the system or the apparatus.

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2020-055973, filed Mar. 26, 2020, which is hereby incorporated by reference herein in its entirety.

What is claimed is:

1. An information processing apparatus, comprising:
a memory storing a program; and
one or more processors which, by executing the program, function as:
an acquisition unit configured to acquire ultrasonic image data;
an inference unit configured to infer a body mark by inputting the ultrasonic image data acquired by the acquisition unit to a classifier based on machine learning, wherein the classifier based on machine learning is a classifier that has undergone learning processing based on supervisory data in which information indicating a type of the body mark is set as a correct label and ultrasonic image data captured in an image-capturing range corresponding to the correct label is set as a ground truth image; and
a display control unit configured to provide the body mark inferred by the inference unit together with the ultrasonic image data.

2. The information processing apparatus according to claim 1,
wherein the inference unit further infers a position of a probe on the body mark from the ultrasonic image data acquired by the acquisition unit, and
wherein the display control unit displays superimposed image data in which a probe mark based on the inferred position of the probe is superimposed on the body mark inferred by the inference unit.

3. The information processing apparatus according to claim 2, wherein the inference unit configured to infer a position of a probe on the body mark by inputting the ultrasonic image data acquired by the acquisition unit to a classifier based on machine learning, wherein the classifier based on machine learning is a classifier that has undergone learning processing based on supervisory data in which information indicating the type of the body mark and the position of the probe on the body mark is set as a correct label and ultrasonic image data captured in an image-capturing range corresponding to the correct label is set as a ground truth image.

4. The information processing apparatus according to claim 1, wherein the inference unit performs inference by a classifier based on machine learning.

5. The information processing apparatus according to claim 4, wherein the classifier based on machine learning is a classifier that has undergone learning processing based on supervisory data in which information indicating a type of the body mark is set as a correct label and ultrasonic image data captured in an image-capturing range corresponding to the correct label is set as a ground truth image.

6. The information processing apparatus according to claim 4, wherein the inference unit outputs an inference result as a likelihood.

7. The information processing apparatus according to claim 6, wherein the display control unit displays the superimposed image data and the likelihood in association with each other.

8. The information processing apparatus according to claim 6, further comprising a determination unit configured to determine whether the result of inference by the inference unit satisfies a predetermined reference,
wherein the display control unit provides display based on a result of determination by the determination unit.

9. The information processing apparatus according to claim 8, wherein the determination unit determines whether at least one of a likelihood corresponding to a class constituting the inference result and a difference between likelihoods respectively corresponding to a plurality of classes satisfies the predetermined reference.

10. The information processing apparatus according to claim 9, wherein the display control unit provides display with a different number of pieces of superimposed image data to be displayed based on the result of determination by the determination unit.

11. The information processing apparatus according to claim 4, wherein the inference unit includes a plurality of classifiers.

12. The information processing apparatus according to claim 11,
wherein the acquisition unit further acquires a type of the probe,
wherein the information processing apparatus further comprises a selection unit configured to select a classifier to perform inference from among the plurality of classifiers constituting the inference unit based on the type of the probe acquired by the acquisition unit, and
wherein the inference unit infers the body mark corresponding to the ultrasonic image data from the ultrasonic image data by using the classifier selected by the selection unit.

13. An information processing method, comprising:
acquiring ultrasonic image data;
inferring a body mark by inputting the acquired ultrasonic image data to a classifier based on machine learning, wherein the classifier based on machine learning is a classifier that has undergone learning processing based on supervisory data in which information indicating a type of the body mark is set as a correct label and ultrasonic image data captured in an image-capturing range corresponding to the correct label is set as a ground truth image; and
displaying the inferred body mark together with the ultrasonic image data.

14. The information processing method according to claim 13,
wherein a position of a probe on the body mark is further inferred from the acquired ultrasonic image data, and
wherein superimposed image data in which a probe mark based on the inferred position of the probe is superimposed on the inferred body mark.

15. A non-transitory computer readable storage medium storing a program for causing a computer to execute the information processing method according to claim 13.

16. An ultrasonic diagnosis apparatus, comprising:
a memory storing a program; and
one or more processors which, by executing the program, function as:
an acquisition unit configured to acquire ultrasonic image data and a type of probe;
a selection unit configured to select a classifier to perform inference from among the plurality of classifiers based on the type of the probe acquired by the acquisition unit;
an inference unit configured to infer a body mark corresponding to the ultrasonic image data by the classifier based on machine learning selected by the selection unit;
a display control unit configured to display the body mark inferred by the inference unit together with the ultrasonic image data.

17. The ultrasonic diagnosis apparatus according to claim 16,
wherein the inference unit further infers a position of a probe on the body mark from the ultrasonic image data acquired by the acquisition unit, and
wherein the display control unit displays superimposed image data in which the probe mark based on the inferred position of the probe is superimposed on the body mark inferred by the inference unit.

* * * * *